(12) United States Patent
Cheng (10) Patent No.: US 11,090,668 B2
(45) Date of Patent: Aug. 17, 2021

(54) SELECTIVE SEALING CARTRIDGE

(71) Applicant: L'Oreal, Paris (FR)

(72) Inventor: Wenzhen Cheng, Clark, NJ (US)

(73) Assignee: L'Oreal, Paris (FR)

( * ) Notice: Subject to any disclaimer, the term of this patent is extended or adjusted under 35 U.S.C. 154(b) by 38 days.

(21) Appl. No.: 16/738,774

(22) Filed: Jan. 9, 2020

(65) Prior Publication Data

US 2021/0213472 A1   Jul. 15, 2021

(51) Int. Cl.
*B05B 11/00* (2006.01)
*A45D 34/00* (2006.01)
*A61M 11/00* (2006.01)
*A61M 35/00* (2006.01)

(52) U.S. Cl.
CPC .......... *B05B 11/0054* (2013.01); *A45D 34/00* (2013.01); *A61M 11/00* (2013.01); *A61M 35/00* (2013.01); *A45D 2034/005* (2013.01); *A45D 2200/057* (2013.01); *A61M 2205/123* (2013.01)

(58) Field of Classification Search
CPC ................ B05B 11/0054; A45D 34/00; A45D 2034/005; A45D 2200/057; A45D 2205/123; A61M 11/00; A61M 35/00
USPC .................................................. 222/325–327
See application file for complete search history.

(56) References Cited

U.S. PATENT DOCUMENTS

| | | | |
|---|---|---|---|
| 5,417,258 A | 5/1995 | Privas | |
| 5,893,515 A * | 4/1999 | Hahn | B05B 11/3028 239/7 |
| 6,364,170 B1 * | 4/2002 | Anderson | B05B 11/0097 222/321.7 |
| 7,699,052 B2 * | 4/2010 | Schiewe | B05B 11/02 128/200.22 |
| 2004/0094146 A1 * | 5/2004 | Schiewe | B05B 11/0054 128/200.11 |
| 2004/0182387 A1 * | 9/2004 | Steiner | A61M 16/0825 128/203.15 |
| 2005/0029307 A1 * | 2/2005 | Py | B65D 81/245 222/386 |

(Continued)

FOREIGN PATENT DOCUMENTS

| | | |
|---|---|---|
| EP | 0546898 B1 | 4/1996 |
| FR | 3049441 B1 | 10/2017 |

(Continued)

*Primary Examiner* — Vishal Pancholi
(74) *Attorney, Agent, or Firm* — Christensen O'Connor Johnson Kindness PLLC (57) ABSTRACT

Cartridges are configurable between a closed state and an open state. The cartridges include a cartridge body and a reservoir disposed in the cartridge body. The cartridge body has an outer locking element, and the reservoir has a rotational locking element. In the closed state, the outer locking element engages the rotational locking element such that the reservoir cannot be rotated out of a first rotational position relative to the cartridge body in which a fluid outlet of the reservoir is not in fluid communication with a fluid outlet of the cartridge body. In the open state, the outer locking element of the cartridge body does not engage the rotational locking element of the reservoir, and the reservoir is in a second rotational position relative to the cartridge body such that the fluid outlet of the reservoir is in fluid communication with the fluid outlet of the cartridge body.

20 Claims, 8 Drawing Sheets

(56) References Cited

U.S. PATENT DOCUMENTS

| | | | |
|---|---|---|---|
| 2009/0206174 A1 | 8/2009 | Arnaud et al. | |
| 2010/0282776 A1* | 11/2010 | Knopow | B67D 7/005 222/145.1 |
| 2013/0158466 A1* | 6/2013 | Kim | H05H 1/2406 604/23 |
| 2013/0327327 A1* | 12/2013 | Edwards | A61M 15/0016 128/203.11 |
| 2016/0158466 A1 | 6/2016 | Brunner et al. | |
| 2018/0127196 A1* | 5/2018 | Edwards | A61M 15/0043 |

FOREIGN PATENT DOCUMENTS

| | | | |
|---|---|---|---|
| WO | 9749620 A1 | 12/1997 |
| WO | 2017174479 A1 | 10/2017 |

* cited by examiner

SELECTIVE SEALING CARTRIDGE

SUMMARY

In an aspect, the present disclosure provides a cartridge configurable between a closed state and an open state. The cartridge includes a cartridge body and a reservoir disposed in the cartridge body. The cartridge body has an outer locking element, and the reservoir has a rotational locking element. In the closed state, the outer locking element engages the rotational locking element such that the reservoir cannot be rotated out of a first rotational position relative to the cartridge body in which a fluid outlet of the reservoir is not in fluid communication with a fluid outlet of the cartridge body. In the open state, the outer locking element of the cartridge body does not engage the rotational locking element of the reservoir, and the reservoir is in a second rotational position relative to the cartridge body such that the fluid outlet of the reservoir is in fluid communication with the fluid outlet of the cartridge body.

In some embodiments, the rotational locking element of the reservoir is configured to be moved in a release direction (e.g., a radially-inward release direction) to an extent that disengages the rotational locking element from the outer locking element. In some embodiments, the rotational locking element is biased toward a radially-outward position. In some embodiments, the rotational locking element of the reservoir is a finger extending in an axial direction from an outer wall of the reservoir. In some embodiments, the outer locking element is an aperture through an outer wall of the cartridge body. In some embodiments, the cartridge body forms an interior channel (e.g., between an outer wall and a collar of the cartridge body) configured to receive the rotational locking element of the reservoir. In some embodiments, the rotational locking element is configured to move within the interior channel during movement between the closed state and the open state. In some embodiments, a neck portion of the reservoir is disposed within a cylindrical collar of the cartridge body. In some embodiments, in the closed state, the fluid outlet of the reservoir forms a fluid-tight seal with an interior surface of the cylindrical collar. In some embodiments, the fluid outlet of the reservoir is disposed on the neck portion. In some embodiments, the cartridge includes a cartridge cap disposed over the cartridge body and the reservoir. In some embodiments, the cartridge includes an identifier configured to convey information about the formulation or the cartridge to a device. In some embodiments, the cartridge includes a formulation stored in the reservoir. In some embodiments, the cartridge body includes an alignment structure (e.g., a concave outer surface of the cartridge body) configured to align the cartridge with a device. In some embodiments, the reservoir includes a coupling structure configured to couple with a complementary coupling structure of a device. In some embodiments, a difference between the first rotational position and the second rotational position is between about 90 degrees and about 180 degrees.

In another aspect, the present disclosure provides systems including a device (e.g., a nebulizer) and a cartridge configured for reversible coupling with the device. The cartridge is configurable between a closed state and an open state, and includes a cartridge body and a reservoir disposed in the cartridge body. The cartridge body has an outer locking element. The reservoir is configured to store a formulation, and has a rotational locking element. In the closed state, the outer locking element of the cartridge body engages the rotational locking element of the reservoir such that the reservoir cannot be rotated out of a first rotational position relative to the cartridge body in which a fluid outlet of the reservoir is not in fluid communication with a fluid outlet of the cartridge body. In the open state, the outer locking element of the cartridge body does not engage the rotational locking element of the reservoir, and the reservoir is in a second rotational position relative to the cartridge body such that the fluid outlet of the reservoir is in fluid communication with the fluid outlet of the cartridge body.

BRIEF DESCRIPTION OF THE SEVERAL VIEWS OF THE DRAWINGS

The foregoing aspects and many of the attendant advantages of the claimed subject matter will become more readily appreciated by reference to the following detailed description, when taken in conjunction with the accompanying drawings, wherein:

DETAILED DESCRIPTION

The present disclosure provides cartridges configured to be selectively and reversibly opened and closed. In one representative application, the inventive cartridges are part of a system configured to deliver a formulation (e.g., a cosmetic, pharmaceutical, or dermatological formulation) in aerosol form onto skin. For example, in one embodiment, the cartridge is a consumable sub-assembly configured for use with a device such as nebulizer. Representative nebulizers include those described in U.S. patent application Ser. No. 15/942,304, which is hereby incorporated by reference in its entirety. However, the inventive cartridges are useful both alone and in connection with additional devices beyond nebulizers. In some embodiments, cartridges of the present system are adapted to other devices, e.g., refillable soap/hand sanitizer/shampoo devices, flavored beverage devices, soft drink fountains, and other fluid dispenser systems.

The inventive cartridges are configured to be reversibly and selectively opened and closed (i.e., sealed), and formulation remaining in the cartridge does not leak from the cartridge when the cartridge is uncoupled from a device and/or closed. Additionally, exposure of formulation within the cartridge to the ambient environment is minimized or prevented entirely when the cartridge is closed, thereby preserving the formulation.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
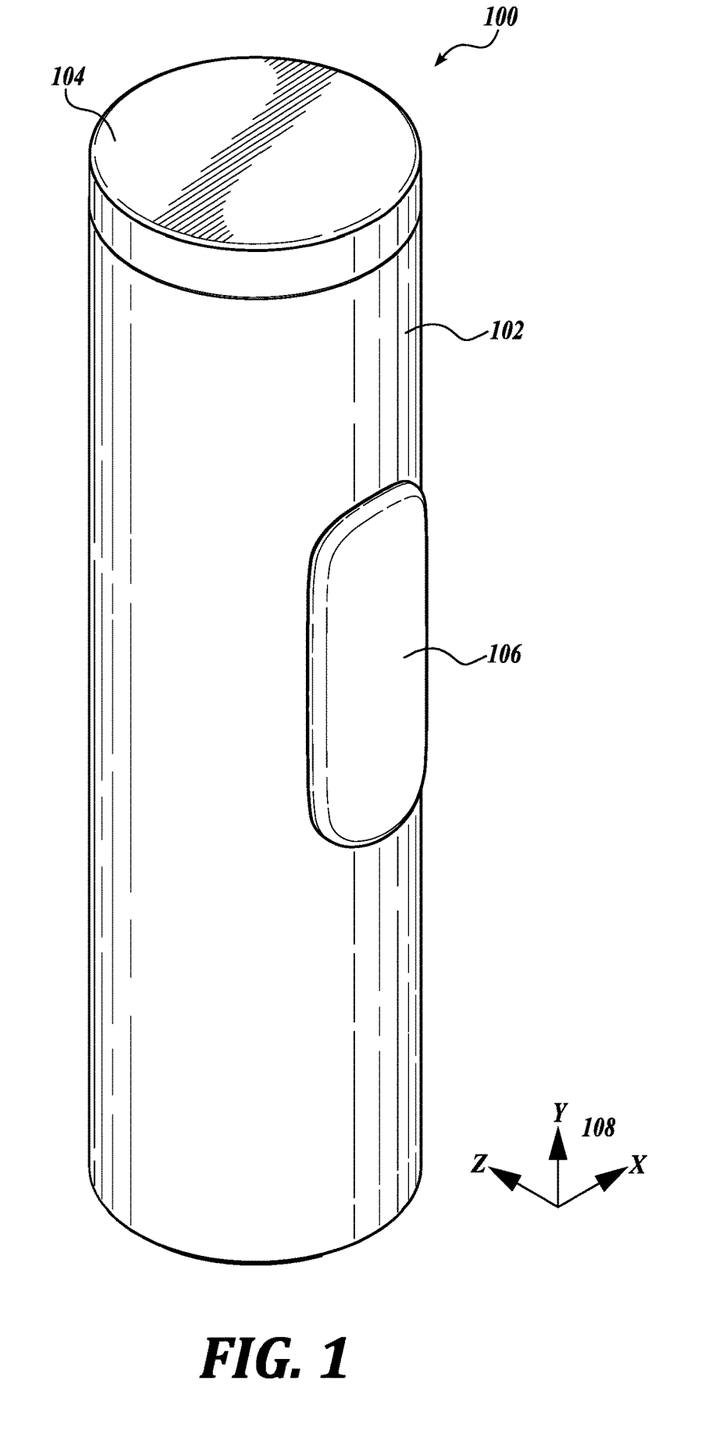
FIG. 1 shows an upper left perspective view of a system in accordance with one representative embodiment of the present disclosure.
Figure 2:
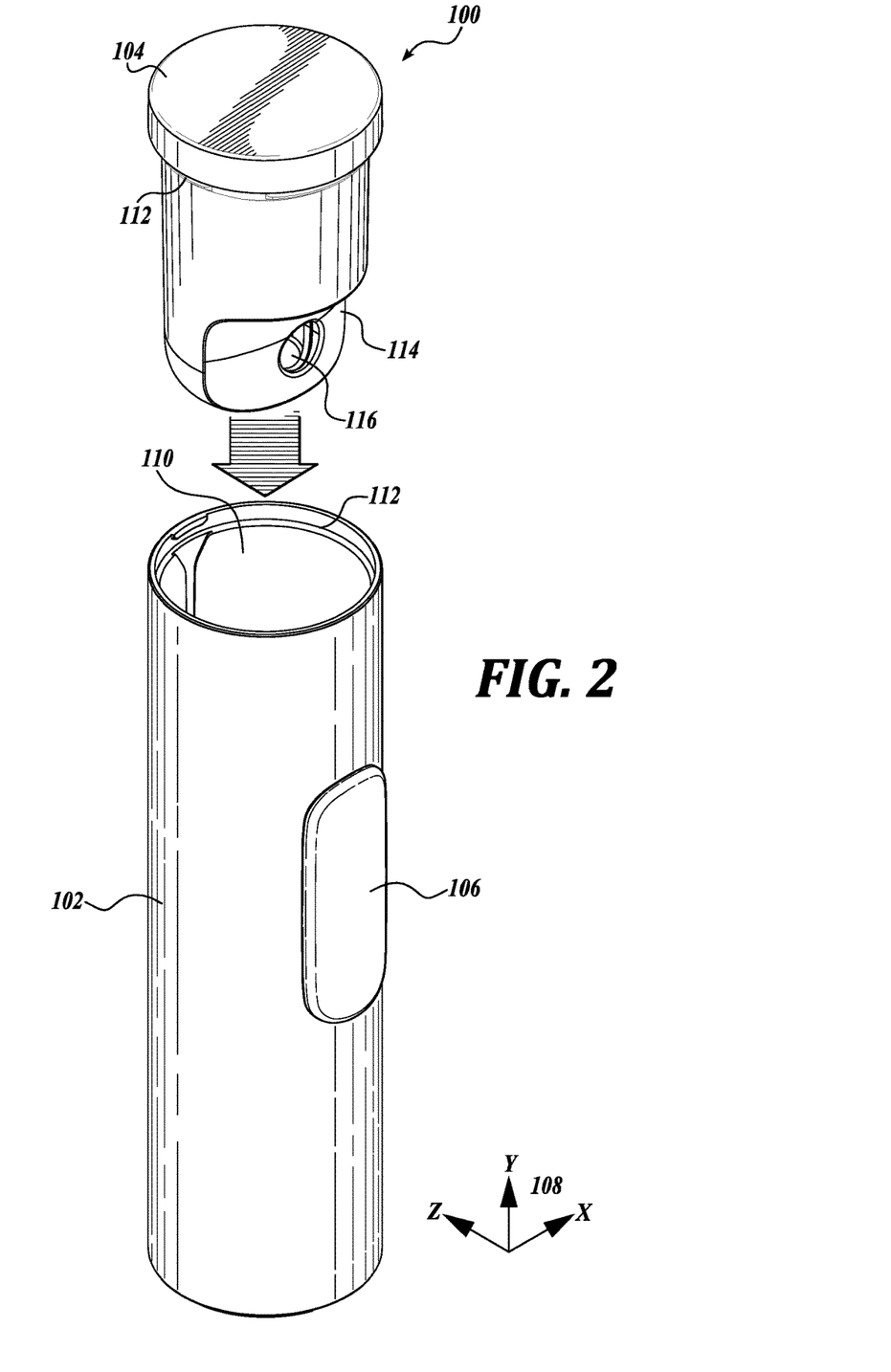
FIG. 2 shows a partially exploded upper left perspective view of the system of FIG. 1.

FIG. 1 and FIG. 2 illustrate a system 100 in accordance with a representative embodiment of the disclosure. System 100 includes a device (in this embodiment, a nebulizer 102) and a cartridge 104 that are reversibly couplable. As used herein, the cartridge 104 is reversibly coupled with the nebulizer 102 when it is securely coupled to the nebulizer 102, but may be removed without damaging either the nebulizer 102 or the cartridge 104. Further, the nebulizer 102 is configured to fluidically couple with a formulation contained within the cartridge 104 such that the nebulizer 102 can selectively discharge an aerosol comprising the formulation. For example, in one representative method of use, a user activates a switch 106, which activates one or more valves and circuitry of a nebulizing assembly contained within the nebulizer 102, thereby causing the nebulizer 102 to discharge an aerosol. Features of the nebulizer 102 and cartridge 104 that enable the fluidic coupling are described below in detail. The nebulizer 102 may be utilized in a system having any of the cartridges described herein.

The coordinate system 108 shown in FIG. 1 and FIG. 2 is used consistently throughout this disclosure, including to characterize section views.

As shown in FIG. 2, cartridge 104 is configured for insertion into an opening 110 of nebulizer 102. The location of opening 110 is representative. In some embodiments, the opening 110 is located on another portion of the nebulizer 102. Cartridge 104 is reversibly coupled within nebulizer 102 such that it can be securely coupled to and selectively released from the nebulizer 102 one or more times. To facilitate this selective coupling, the representative cartridge 104 includes at least one coupling structure 112 disposed on an outer surface thereof. Accordingly, the nebulizer 102 includes at least one complementary coupling structure 112. In FIG. 1, the coupling structures 112 include a detent and a recess. In some embodiments the nebulizer 102 and the cartridge 104 include other cooperatively-coupling structures, such as threads, latches, magnets, and the like. To facilitate correctly-aligned insertion of the cartridge 104 into the nebulizer 102 such that a fluid outlet 116 of the cartridge 104 has the correct orientation with respect to the nebulizer 102, the cartridge 104 and the nebulizer 102 include complementary alignment structures 114. In the representative embodiment of FIG. 2, the alignment structure 114 of the cartridge 104 includes a concave outer surface, which is sized and dimensioned to have a complementary fit with a convex interior portion of the nebulizer 102 (see, e.g., alignment structure 706 of FIG. 7). In some embodiments the alignment structures 114 includes other structures, such as a track and channel, a detent and recess, and/or the like.

FIGS. 3A-FIG. 5 show different views of a representative cartridge 300 configured for selective and reversible coupling with a device, such as the nebulizer 102 of FIG. 1. The cartridge 300 is configurable between an open state and a closed state. In the closed state, the cartridge 300 is configured to prevent dispensation or leakage of a formulation. In the open state, the cartridge 300 is configured to dispense formulation, e.g., to a device such as the nebulizer 102 of FIG. 1. To control movement between the closed state and the open state, the cartridge 300 includes a rotational locking system, which is described below in detail.

FIGS. 3A and 3B show exploded views of the cartridge 300 in a closed state. Cartridge 300 includes three main components: a cartridge body 302, a reservoir 304, and a cartridge cap 306. In some embodiments the reservoir 304 and the cartridge cap 306 are formed as a single component. The rotational locking system, described below, generally controls relative rotational movement of the reservoir 304 and the cartridge cap 306 about axis 308 relative to the cartridge body 302, between a first rotational position and a second rotational position.

Cartridge body 302 houses and protects the reservoir 304 and the formulation stored therein, and also provides elements of the rotational locking system. Cartridge body 302 has a hollow, open-ended shape with a first end 310 and a second end 312, the first end 310 being configured for insertion into a device before the second end 312. As used herein, the first end 310 and second end 312 may be used to orient description of other aspects of the cartridge 300, not just the cartridge body 302. The second end 312 is open-ended and configured to be enclosed by a cartridge cap 306 that couples with cartridge body 302. In some embodiments, cartridge body 302 is formed from a thermoplastic polymer such as polypropylene, polyethylene, or the like. Representative materials are resistant to fatigue failure, have high resistance to creep, and have relatively high strength.

In the representative embodiment of FIGS. 3A and 3B, cartridge body 302 is generally cylindrical to facilitate insertion into a cylindrical device (e.g., the nebulizer 102 of FIG. 1). Accordingly, cartridge body 302 has an annular outer wall 314. The annular outer wall 314 includes features that form part of the rotational locking system, including an outer locking element (see outer locking element 342 shown in FIG. 4). In some embodiments, cartridge body 302 is another shape, e.g., rectangular, conical, oval-shaped, and the like. In the representative embodiment of FIGS. 3A and 3B, the outer wall 314 includes a concave alignment structure 316 located proximate to the first end 310, to facilitate alignment of a fluid outlet 318 with a corresponding fluid outlet or nozzle of a device. A liquid control valve (e.g., a diaphragm-type valve, such as may be formed from silicone, rubber, or the like) is fitted into the fluid outlet 318 of the cartridge body 302. In some embodiments, the alignment structure 316 is located proximate to the second end 312 or at an intermediate position along cartridge body 302. In some embodiments, the alignment structure 316 has a different shape or size than shown in FIGS. 3A and 3B.

Reservoir 304 is a substantially hollow body disposed within (i.e., nested within) the cartridge body 302, and is configured to store a formulation (e.g., a liquid cosmetic, pharmaceutical, or dermatological formulation). Accordingly, reservoir 304 includes an outer wall 320 having a smaller diameter than the outer wall 314 of the cartridge body 302. In some embodiments the reservoir 304 is configured to store about 5 ml to about 50 ml of a liquid formulation, e.g., about 15 ml or any other volume in that range.

Figure 3A:
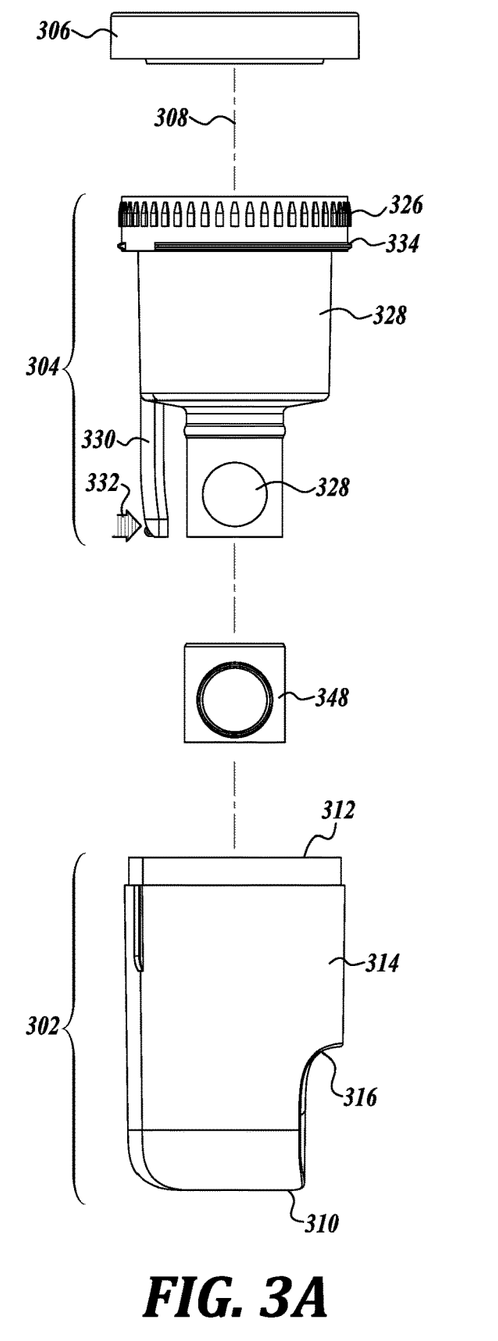
FIG. 3A shows an exploded left elevation view of a cartridge in a closed state in accordance with one representative embodiment of the present disclosure.
Figure 3B:
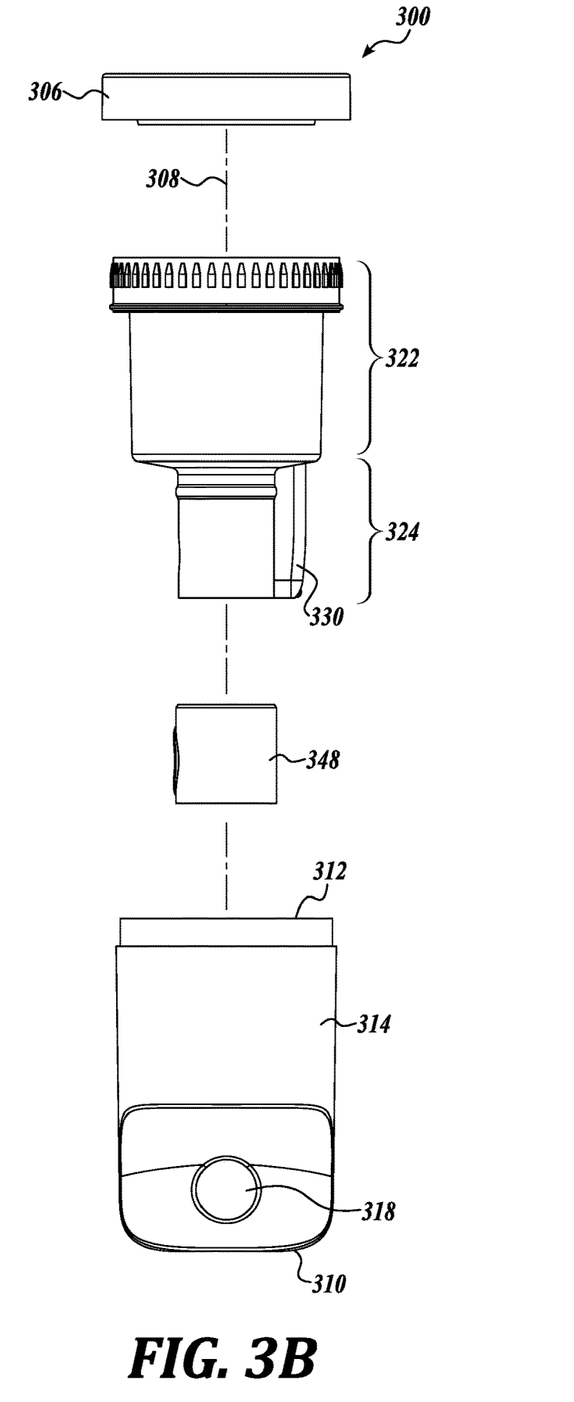
FIG. 3B shows an exploded front elevation view of the cartridge of FIG. 3A.

Reservoir 304 includes a main portion 322 and a neck portion 324, both of which are substantially hollow, in fluid communication with each other, and are configured to store the formulation. The main portion 322 has an open-ended shape which is configured to be enclosed by the cartridge cap 306. The main portion 322 also includes engagement members 326 that are configured to retain cartridge cap 306 on the reservoir 304, and to facilitate rotation of the reservoir 304 within the cartridge body 302 by rotating the cartridge cap 306. Neck portion 324 has a narrower diameter than the main portion 322, and is configured to fit within (and to rotate within) a cylindrical collar of the cartridge body 302 (described below). Neck portion 324 includes a fluid outlet 328, which in some embodiments is fitted with a liquid control valve (e.g., a diaphragm-type valve, such as may be formed from silicone, rubber, or the like). In some embodiments, the neck portion 324 is fitted with an optional gasket or sealing shroud 348 to form a fluid tight seal with the cartridge body 302. In the closed state, the reservoir 304 is in a first rotational position relative to the cartridge body 302 in which the fluid outlet 328 of the reservoir 304 is not in fluid communication with the fluid outlet 318 of the cartridge body 302, and consequently no formulation can be dispensed from the cartridge 300. In some embodiments, the fluid outlet 328 of the cartridge body 302 forms a fluid-tight seal with an interior surface of the collar in the closed state. On the other hand, in the open state, the cartridge body 302 is in a second rotational position relative to the reservoir 304 such that the fluid outlet 328 of the reservoir 304 is in fluid communication with the fluid outlet 318 of the cartridge body 302, such that formulation can be dispensed from the cartridge 300. Reservoir 304 is substantially formed from a single piece (e.g., an injection molded thermoplastic piece), but may be formed from two or more pieces in some embodiments.

Figure 5A:
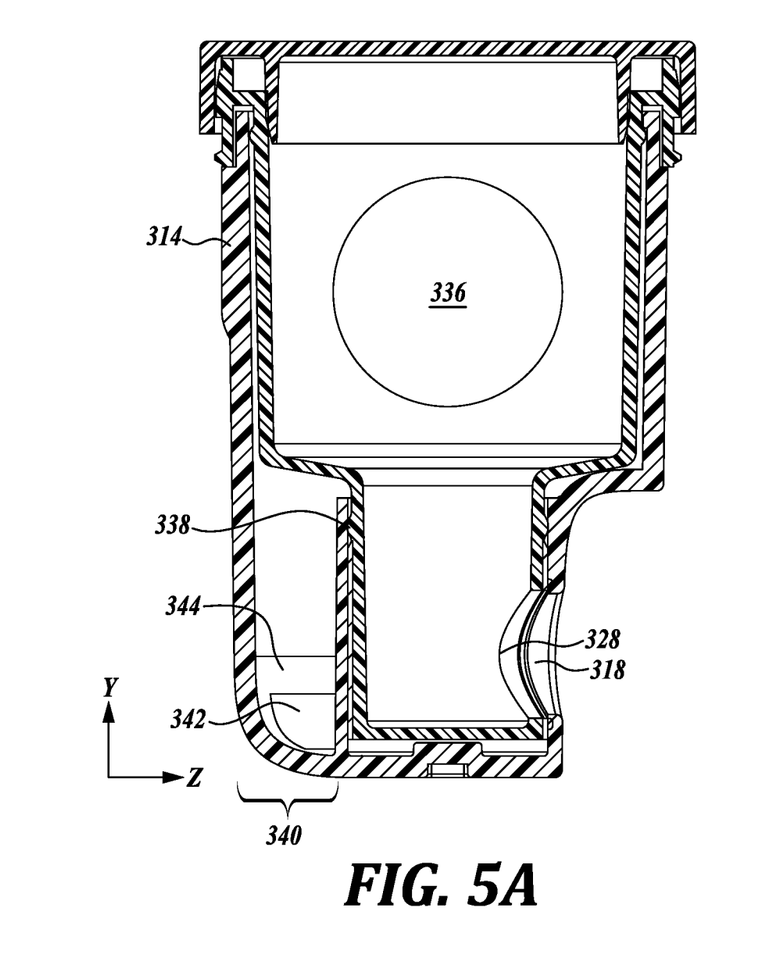
FIG. 5A shows a left side section view of the cartridge of FIG. 3A in an open state.
Figure 5B:
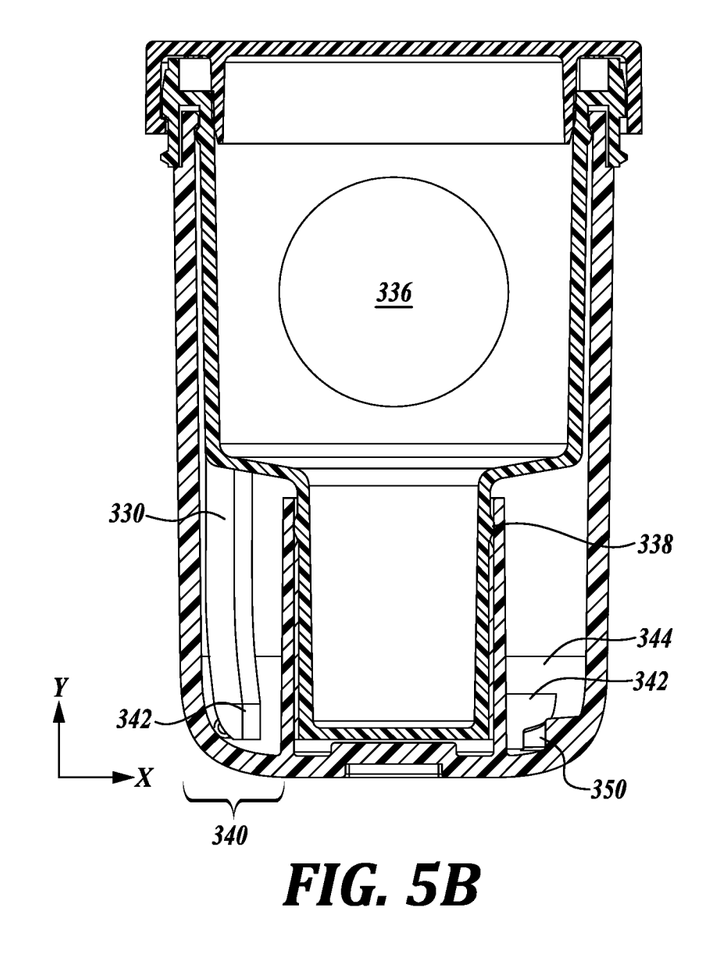
FIG. 5B shows a front side section view of the cartridge of FIG. 3A in the open state.

A rotational locking element 330 is disposed on the outer wall 320 of reservoir 304, and forms part of the rotational locking system. In the representative embodiment of FIG. 3A—FIG. 5, the rotational locking element 330 is a level— in this example, a finger extending straight downward and generally parallel to the axis 308 (i.e., in an axial direction). In some embodiments, the rotational locking element 330 is a button, a bulge, a lever, a latch, or the like. The rotational locking element 330 is configured to selectively engage an outer locking element of the cartridge body 302, as described in greater detail below. For example, the rotational locking element 330 of FIG. 3A—FIG. 5 is configured to engage the outer locking element of the cartridge body 302 when the cartridge 300 is in the closed state shown. That is, the rotational locking element 330 extends straight down and into the outer locking element of the cartridge body 302, as described below. Further, the rotational locking element is configured to bend radially inward and disengage the outer locking element of the cartridge body when the cartridge 300 is in the open state (as shown in FIG. 5), i.e., when the rotational locking element 330 is moved in a release direction 332, which in this embodiment is radially inward and substantially perpendicular to the axis 308. Thus, when the rotational locking element 330 is moved in the release direction 332 and clears the outer locking element, the reservoir 304 may be rotated within the cartridge body 302 between the first rotational position and the second rotational position. In some embodiments, a difference between the first rotational position and the second rotational position is about 10 degrees to about 350 degrees, or about 90 degrees to about 180 degrees. In some embodiments, the difference between the first rotational position and the second rotational position is about 60 degrees, about 90 degrees, about 120 degrees, or about 180 degrees.

Figure 4:
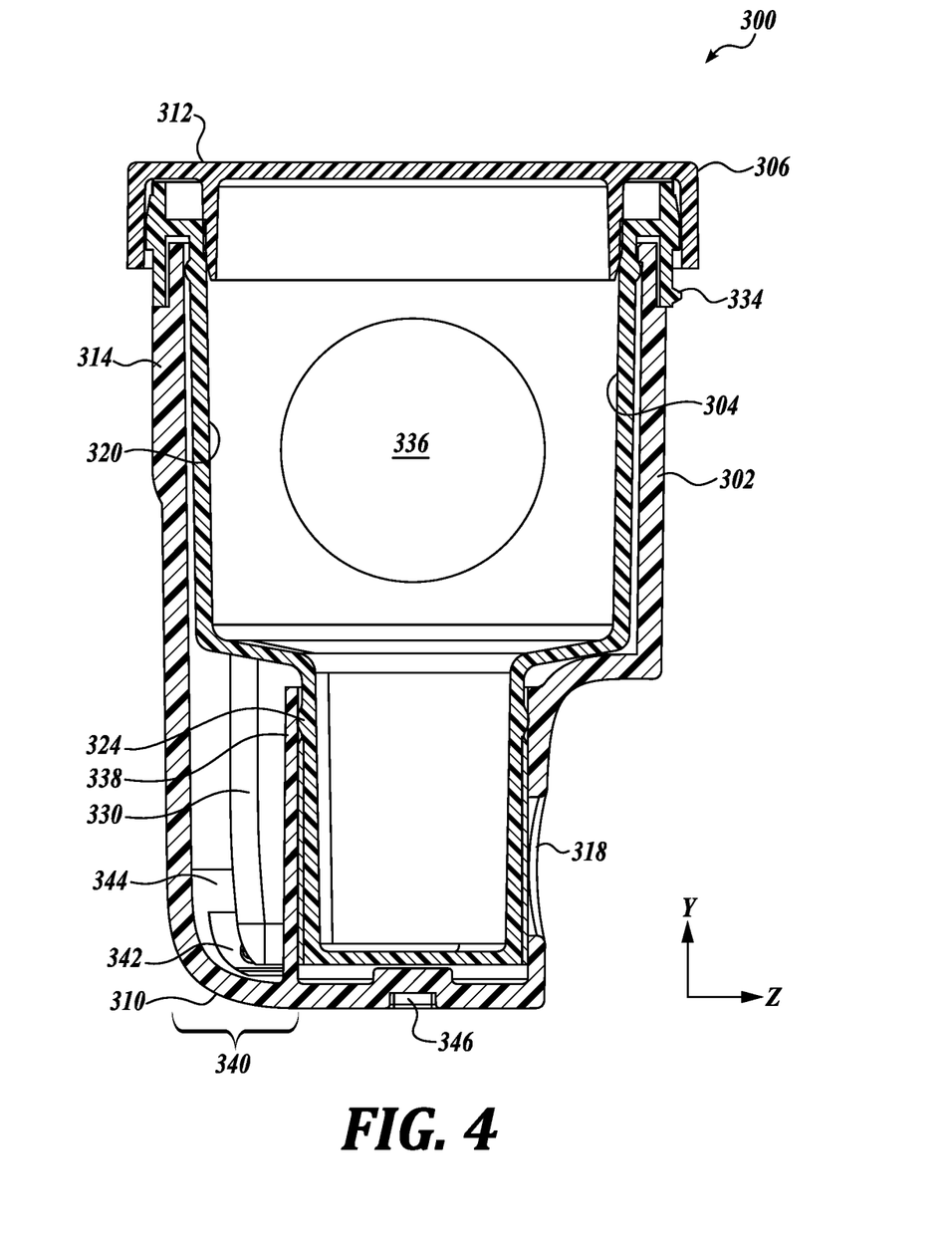
FIG. 4 shows a left side section view of the cartridge of FIG. 3A in a closed state.

Cartridge cap 306 is formed from a similar material as cartridge body 302, and encloses a number of elements within the cartridge body 302, namely the reservoir 304 and the formulation (as shown in FIG. 4). Cartridge cap 306 also acts as a handle configured to rotate the reservoir 304 within the cartridge body 302, as described below. Cartridge cap 306 has an annular outer wall that fits over the open second end 312 of the cartridge body 302 and over the reservoir 304. In some embodiments, the cartridge cap 306 is configured to fit within the open second end 312 of the cartridge body 302, rather than or in addition to over it. Cartridge cap 306 and reservoir 304 include complementary engagement members 326 in order to retain cartridge cap 306 on the reservoir 304, and to facilitate rotation of the reservoir 304 within the cartridge body 302 by rotating the cartridge cap 306. In some embodiments, cartridge cap 306 and reservoir 304 are configured to be a permanent assembly. In some embodiments, engagement members 326 are configured such that cartridge cap 306 can be selectively decoupled from reservoir 304.

FIG. 4 shows a section view in the Y-Z plane of the cartridge 300 of FIG. 3A, in the closed state. As readily seen, the cartridge cap 306 encloses the open ends of the cartridge body 302 and the reservoir 304. Additionally, it can be seen that the reservoir 304 stores a volume of formulation 336, which is shown schematically. It is evident that the cartridge 300 is in the closed state because the wall of neck portion 324 blocks the fluid outlet 318 of the cartridge body 302, thereby indicating that the fluid outlet 318 of the cartridge body 302 is not in fluid communication with the fluid outlet 328 of the reservoir 304. In this closed state, the reservoir 304 is in the first rotational position relative to the cartridge body 302.

From the section view of FIG. 4, additional features of the cartridge 300 become apparent. For example, cartridge body 302 receives the reservoir 304 in a nested configuration, such that the neck portion 324 of the reservoir 304 is disposed within a cylindrical collar 338 of the cartridge body 302. In the closed state, the fluid outlet 328 of the cartridge body 302 forms a fluid-tight seal with an interior surface of the collar 338. Additionally, the reservoir 304 fits over the open second end 312 of the cartridge body 302. Restated, the outer wall 320 of the reservoir 304 forms a track that receives the outer wall 314 of the cartridge body 302. Together, these features enable the reservoir 304 to be rotated relative to the cartridge body 302 while maintaining alignment between the cartridge body 302 and the reservoir 304. Further, reservoir 304 includes coupling structure 334 formed therein, to facilitate selective and secure coupling with a device such as the nebulizer 102 of FIG. 1.

FIG. 4 also shows additional features of the rotational locking system. One aspect is that the outer wall 314 and the collar 338 of the cartridge body 302 form an interior channel 340 having a generally annular shape and extending around a portion of the cartridge body 302. The rotational locking element 330 of the reservoir 304 extends into this interior channel 340 and, during rotation between the closed state to the open state, moves within this interior channel 340 without obstruction from other aspects of the cartridge 300. The interior channel 340 determines the extent to which the reservoir 304 can be rotated within the cartridge body 302, i.e., a difference between a first rotational position (closed state) and a second rotational position (open state). In some embodiments, the difference between the first rotational position and the second rotational position is about 10 degrees to about 350 degrees, or about 90 degrees to about 180 degrees. In some embodiments, the difference between the first rotational position and the second rotational position is about 60 degrees, about 90 degrees, about 120 degrees, or about 180 degrees. A stop may be located at one or more ends of the interior channel 340 to delimit this maximum rotational angle.

Another aspect of the rotational locking system is an outer locking element 342 formed in the outer wall 314 of the cartridge body 302, proximal to the first end 310. Generally, the outer locking element 342 is an aperture, a recess, a stop, or the like, that is formed in the cartridge body 302 and is configured to lockingly receive the rotational locking element 330 of the cartridge body 302 in the closed state. In this representative embodiment, the outer locking element 342 is an aperture formed in the outer wall 314 of the cartridge body 302. The rotational locking element 330 of the reservoir 304 is biased toward the straight-down/radially-outward position shown in FIG. 4 (e.g., by its material properties), such that in the closed state shown, the rotational locking element 330 of the reservoir 304 extends through the outer locking element 342 of the cartridge body 302 (i.e., through the aperture). In the non-limiting representative embodiment of FIG. 3A-FIG. 5, the rotational locking element 330 is formed of a thermoplastic polymer, the properties of which bias the rotational locking element 330 radially outward in the closed state, i.e., prevent the rotational locking element 330 from being pushed radially inward. Consequently, the edges of the outer locking element 342 form stops that block rotational movement of the rotational locking element 330 so long as it extends therethrough, thereby preventing rotational movement of the reservoir 304 relative to the cartridge body 302. In some embodiments, the outer locking element 342 of the reservoir 304 may not be an aperture, but is instead a stop, a shoulder(s), a recess, or the like formed integrally with the outer wall 314 of the cartridge body 302 (e.g., an inner surface 344 of the outer wall 314). It is advantageous for the outer locking element 342 to be formed as an aperture however, because an external device (such as an unlocking member of the nebulizer 102 of FIG. 1) can extend through the aperture in order to move the rotational locking element 330 out of the closed state. This functionality is described below with respect to FIG. 7 and FIG. 8.

Figure 6A:
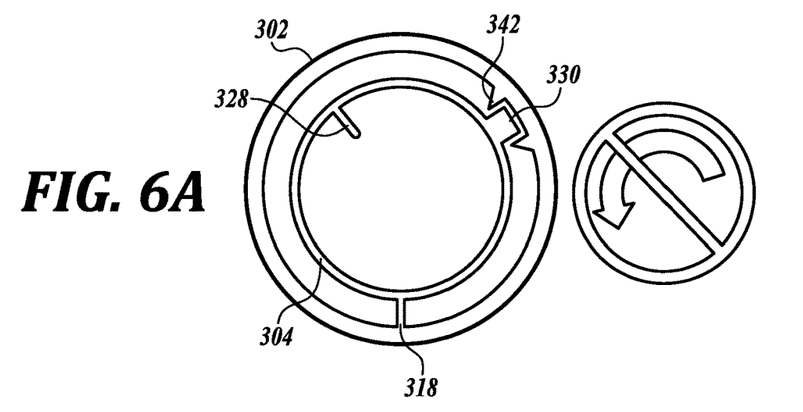
FIG. 6A shows a schematic cartridge in a closed state, in accordance with one representative embodiment of the present disclosure.
Figure 6B:
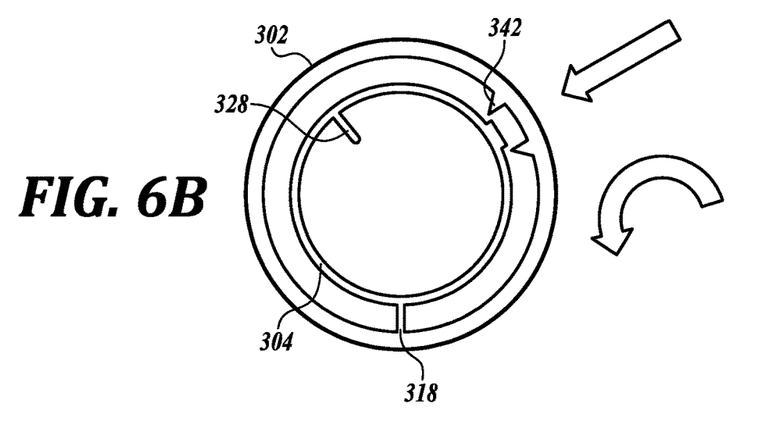
FIG. 6B shows the schematic cartridge of FIG. 6A transitioning from the closed state to an open state, in accordance with one representative embodiment of the present disclosure.
Figure 6C:
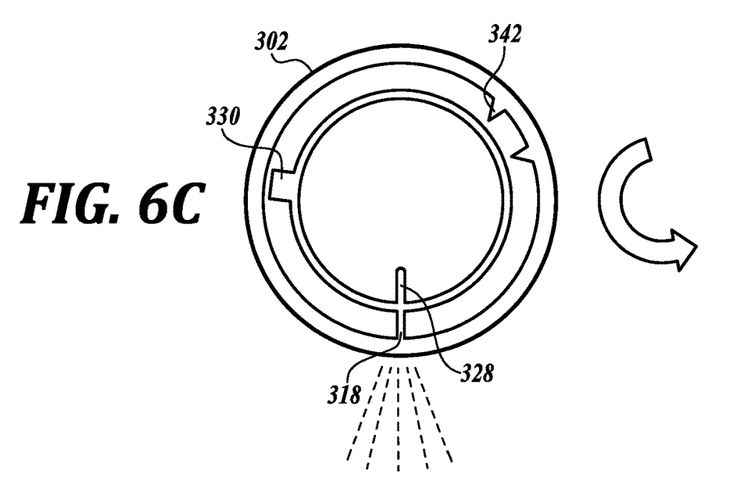
FIG. 6C shows the schematic cartridge of FIG. 6A in the open state, in accordance with one representative embodiment of the present disclosure.

Another aspect of the cartridge 300 is the optional identifier 346 located in the outer wall 314 of the cartridge body 302 proximal to the first end 310 thereof. The identifier 346 is configured to convey information to a device (e.g., the nebulizer 102) about the formulation 336 stored within the cartridge 300. In FIG. 4, the identifier 346 is an electronic component configured to output information pertaining to the formulation 336, such as: formulation type, manufacture date, expiration date, aerosol dispensation volume, and the like. In some embodiments, the identifier 346 is a mechanical identifier having one or more mechanical features (e.g., one or more fingers or raised portions) that correspond with information about the formulation 336. For example, in some embodiments, a device includes one or more switches configured to receive the identifier 346 and to determine information about the formulation 336 based upon the one or more mechanical features. In some embodiments, the identifier 346 is located on another part of the cartridge 300, for example proximal to the second end 312 thereof or in the cartridge cap 306.

FIG. 5A and FIG. 5B show section views of the cartridge 300 of FIG. 3A, in the open state, after the reservoir 304 has been rotated relative to the cartridge body 302 from the first rotational position to the second rotational position, e.g., according to a sequence shown and described with respect to FIG. 6A—FIG. 6C. To illustrate different aspects of the cartridge 300, FIG. 5A is taken in the Y-Z plane, whereas FIG. 5B is taken in the X-Y plane. It is evident that the cartridge 300 is in the open state because the fluid outlet 318 of the cartridge body 302 is aligned with and in fluid communication with the fluid outlet 328 of the reservoir 304, thus allowing the formulation 336 to flow out of the cartridge 300.

Viewed together, FIG. 5A and FIG. 5B illustrate differences between the closed state and the open state. Referring to FIG. 5A, it can be seen that the rotational locking element 330 of the reservoir 304 no longer extends through the outer locking element 342 of the cartridge body 302. This is because the rotational locking element 330 has been moved out of the way of, and then rotated relative to, the outer locking element 342. Indeed, FIG. 5B shows that the rotational locking element 330 is located at a circumferentially distant location within the interior channel 340. In the representative embodiment shown, the rotational locking element 330 rests against the inner surface 344 of the cartridge body 302, because it is biased toward the radially-outward position shown in FIG. 4. In some embodiments, the radially outward biasing force of the rotational locking element 330 is tuned to provide a particular resistance and "feel" when moving the cartridge 300 between the closed state and the open state. In some embodiments, the rotational locking element 330 does not contact the inner surface 344 of the cartridge body 302. FIG. 5B also shows a shoulder 350 formed integrally with the cartridge body 302, which limits rotational motion of the rotational locking element 330 within the interior channel 340. In some embodiments, the shoulder 350 is part of the outer locking element 342.

FIG. 6A-FIG. 6C show a schematic and method of transitioning the cartridge 300 between the closed state and the open state.

FIG. 6A shows the cartridge 300 in the closed state (i.e., in the first rotational position relative to the cartridge body 302), in which no formulation can be dispensed therefrom. The closed state is evidenced by two characteristics. First, the fluid outlet 318 of the cartridge body 302 is not in alignment with, or in fluid communication with, the fluid outlet 328 of the reservoir 304. Second, the outer locking element 342 of the cartridge body 302 engages the rotational locking element 330 of the cartridge body 302, thereby preventing relative rotation of the cartridge body 302 and the reservoir 304.

FIG. 6B shows activation of the rotational locking element 330 by a radially inward force F, which moves the rotational locking element 330 in a radially inward release direction such that it clears the outer locking element 342. When the rotational locking element 330 clears the outer locking element 342, the reservoir 304 may be rotated relative to the cartridge body 302. In embodiments where the outer locking element 342 is biased toward the radially-outward position, the rotation should be commenced while the radially inward force F is applied to the rotational locking element 330 and continued until the rotational locking element 330 is clear of the outer locking element 342 in the circumferential direction.

FIG. 6C shows the cartridge 300 in the open state (i.e., in the second rotational position relative to the cartridge body 302), after the cartridge body 302 has been rotated relative to the reservoir 304 such that the fluid outlet 318 is aligned with and in fluid communication with the fluid outlet 328. In this position, the rotational locking element 330 is located at a circumferentially distant location from the rotational locking element 330.

Figure 7:
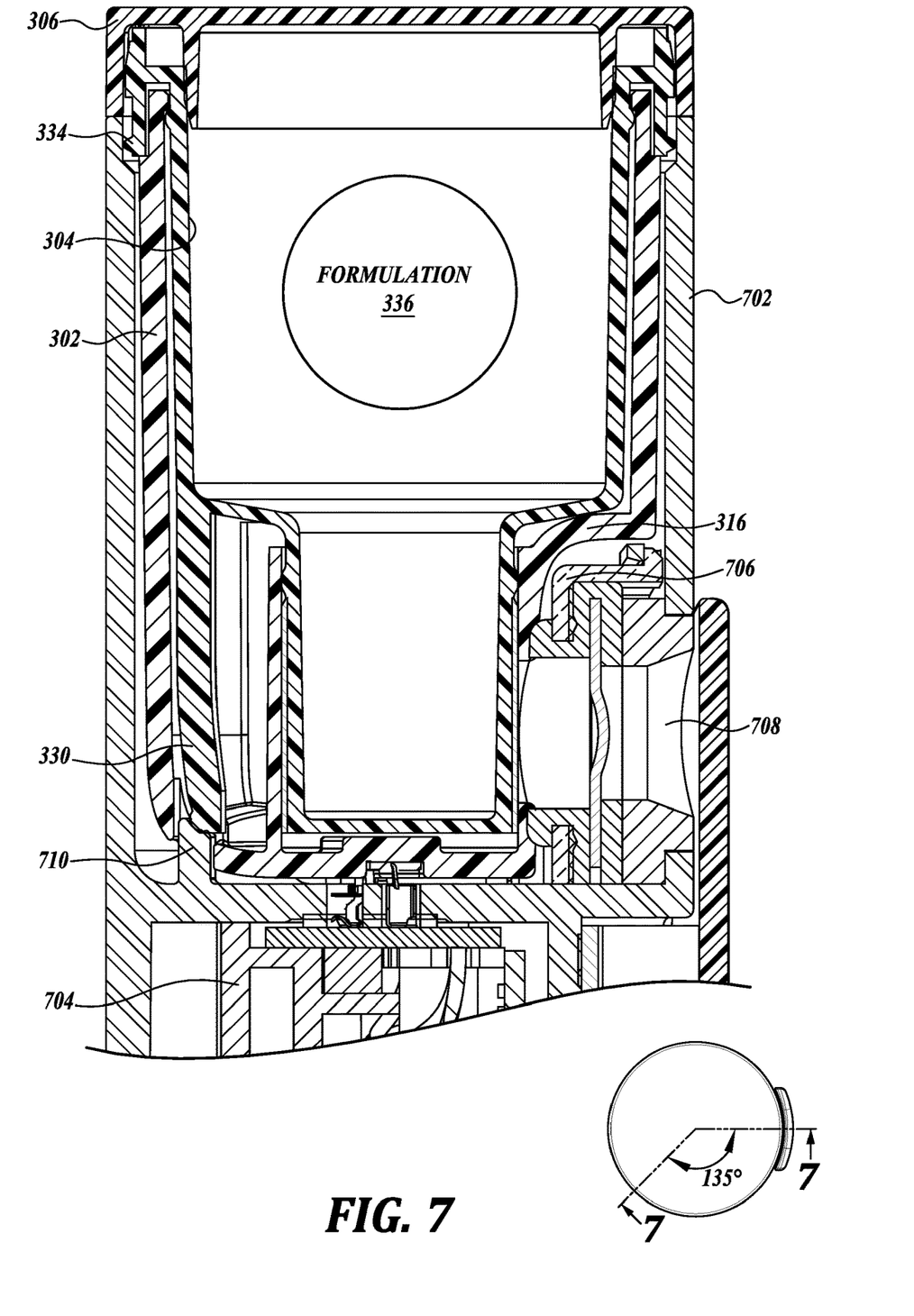
FIG. 7 shows a left side elevation angled section view of a system having a cartridge in a closed state, in accordance with one representative embodiment of the present disclosure.
Figure 8:
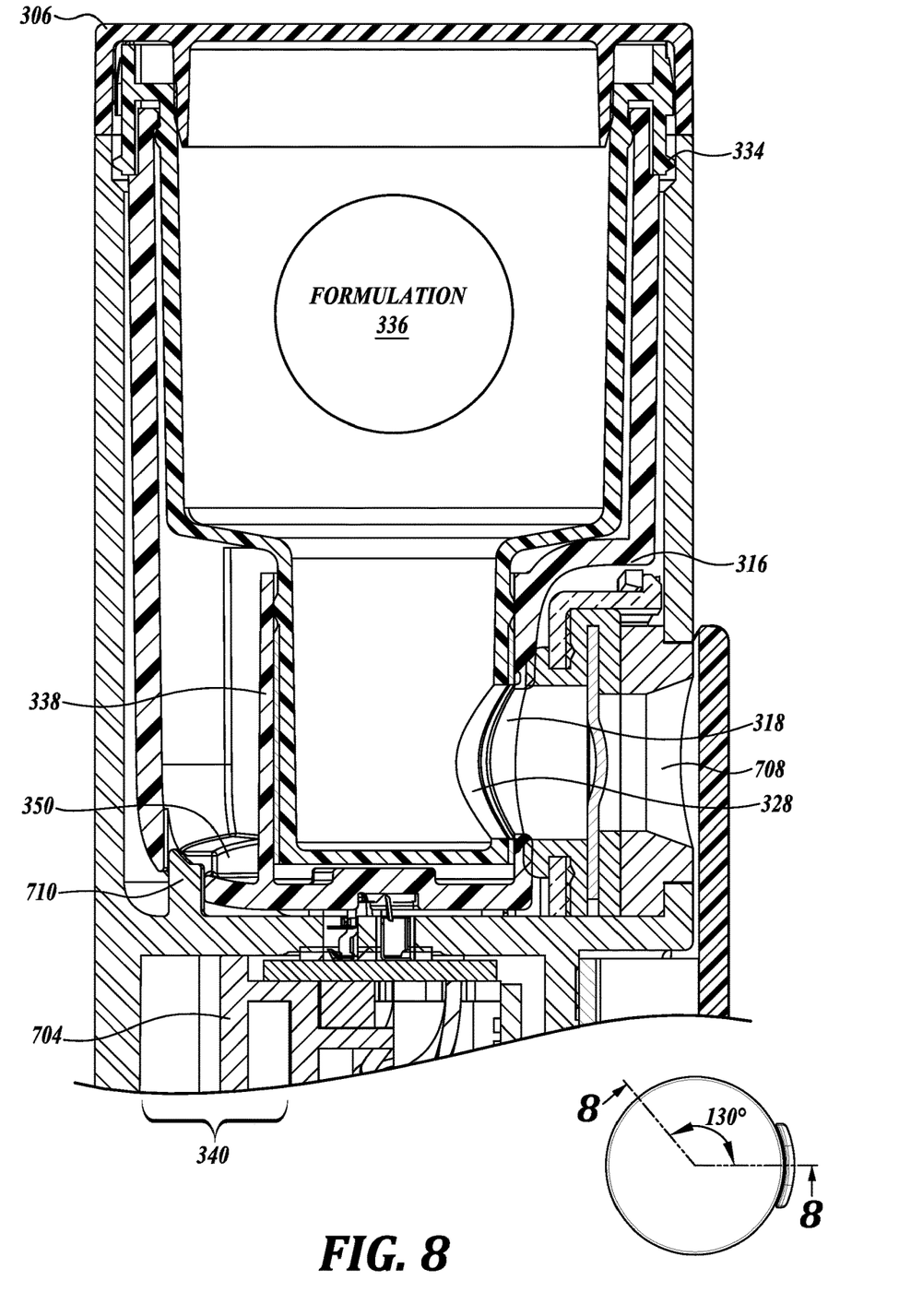
FIG. 8 shows a left side elevation angled section view of the system of FIG. 7, wherein the cartridge is in an open state, in accordance with one representative embodiment of the present disclosure.

FIG. 7 and FIG. 8 show angled section views of the cartridge 300 of FIG. 3A—FIG. 5B coupled with a portion of a device (in this representative embodiment, a nebulizer 702 that is similar to the nebulizer 102 of FIG. 1). In FIG. 7, the cartridge 300 is in the closed state. In FIG. 8, the cartridge 300 is in the open state. Nebulizer 702 includes a nebulizing assembly 704 that forms a reversible fluidic connection with cartridge 300 such that, when the cartridge 300 is in the open state, the nebulizing assembly 704 is configured to receive formulation 336 from the cartridge 300 and discharge it as an aerosol from a nozzle 708. In some embodiments, nebulizer 702 includes at least some features of the nebulizer 102 of FIG. 1. The nebulizing assembly 704 may be an electromechanical assembly having circuitry that is electrically connected to a power source.

Referring to FIG. 7, the cartridge 300 is reversibly and selectively coupled within a hollow cavity of the nebulizer 702. The coupling structure 334 of the cartridge 300 engages complementary coupling structure of the nebulizer 702. Likewise, concave alignment structure 316 of the cartridge 300 is positioned adjacent to complementary alignment structure 706 of the nebulizer 702, to facilitate alignment and fluid communication between the fluid outlets of the cartridge 300 with the nebulizing assembly 704 when the cartridge 300 is in the open state. The alignment structure 316 also holds the cartridge body 302 stationary relative to the nebulizer 702, such that the cartridge 300 can be moved between the closed state and the open state by rotating the cartridge cap 306.

The nebulizer 702 has an unlocking member 710 that is configured to disengage the rotational locking element 330 of the reservoir 304 from the outer locking element 342 of the cartridge body 302. In the representative embodiment of FIG. 7, the unlocking member 710 is a detent having a sloped tip. When the cartridge 300 is fully inserted into the nebulizer 702, the unlocking member 710 extends through the outer locking element 342 of the cartridge body 302 (i.e., through the aperture), and moves the rotational locking element 330 in a radially-inward release direction (due to its sloped tip) until the rotational locking element 330 clears the outer locking element 342. Thus, as long as the cartridge 300 remains fully engaged in the nebulizer 702, the rotational locking element 330 is released from the outer locking element 342 (by the unlocking member 710) and the cartridge 300 can be moved between the closed state and the open state. In some embodiments, the unlocking member 710 is a probe, a lever, or similar mechanical element configured to move the rotational locking element 330 in the release direction. In some embodiments, the unlocking member 710 is a magnet or an electronic component configured to act on the rotational locking element 330 electronically.

FIG. 8 is similar to FIG. 7, except that the cartridge 300 is in the open state, which is evident because the fluid outlet 328 of the reservoir 304, the fluid outlet 318 of the cartridge body 302, and the nozzle 708 are all aligned and in fluid communication. The cartridge 300 has been moved from the closed state to the open state by a sequence such as shown in FIG. 6A—FIG. 6C. It can be seen that the rotational locking element 330 does not extend through the outer locking element 342 (i.e., the aperture) of the cartridge body 302. It can also be seen that the unlocking member 710 of nebulizer 702 is no longer in contact with the rotational locking element 330. Indeed, the rotational locking element 330 has been rotated within the interior channel 340 of the cartridge body 302 to a circumferentially remote location. In this open state, the nebulizer 702 can draw formulation 336 from the cartridge 300 and dispense an aerosol.

Thus, the cartridges of the present disclosure advantageously provide for selective and reversible coupling with devices such as nebulizers, and furthermore provide selective opening and closing, thereby enable secure storage of formulations stored therein.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

In an embodiment, circuitry includes one or more ASICs having a plurality of predefined logic components. In an embodiment, circuitry includes one or more FPGA having a plurality of programmable logic components. In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operatively connected via wireless communication. In an embodiment, remotely located components are operatively connected via one or more receivers, transmitters, transceivers, or the like.

An embodiment includes one or more data stores that, for example, store instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operatively connected to at least one computing device to control (electrical, electromechanical, software-implemented, firmware-implemented, or other control, or combinations thereof) one or more aspects of the embodiment.

In an embodiment, circuitry includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. The term "based upon" means "based at least partially upon."

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

What is claimed is:

1. A cartridge configurable between a closed state and an open state, the cartridge comprising:
   a cartridge body having an outer locking element disposed thereon; and
   a reservoir disposed in the cartridge body and configured to store a formulation, the reservoir having a rotational locking element disposed thereon;
   wherein in the closed state, the outer locking element of the cartridge body engages the rotational locking element of the reservoir such that the reservoir cannot be rotated out of a first rotational position relative to the cartridge body in which a fluid outlet of the reservoir is not in fluid communication with a fluid outlet of the cartridge body,
   wherein in the open state, the outer locking element of the cartridge body does not engage the rotational locking element of the reservoir, and the reservoir is in a second rotational position relative to the cartridge body such that the fluid outlet of the reservoir is in fluid communication with the fluid outlet of the cartridge body.

2. The cartridge of claim 1, wherein the rotational locking element of the reservoir is configured to be moved in a release direction to an extent that disengages the rotational locking element from the outer locking element.

3. The cartridge of claim 2, wherein the release direction is a radially inward release direction.

4. The cartridge of claim 3, wherein the rotational locking element is biased toward a radially-outward position.

5. The cartridge of claim 1, wherein the rotational locking element of the reservoir is a finger extending in an axial direction from an outer wall of the reservoir.

6. The cartridge of claim 5, wherein the outer locking element is an aperture through an outer wall of the cartridge body.

7. The cartridge of claim 1, wherein the cartridge body forms an interior channel configured to receive the rotational locking element of the reservoir.

8. The cartridge of claim 7, wherein the interior channel is formed between an outer wall and a collar of the cartridge body.

9. The cartridge of claim 7, wherein the rotational locking element is configured to move within the interior channel during movement between the closed state and the open state.

10. The cartridge of claim 7, wherein a neck portion of the reservoir is disposed within a cylindrical collar of the cartridge body.

11. The cartridge of claim 10, wherein in the closed state, the fluid outlet of the reservoir forms a fluid-tight seal with an interior surface of the cylindrical collar.

12. The cartridge of claim 10, wherein the fluid outlet of the reservoir is disposed on the neck portion.

13. The cartridge of claim 1, further comprising a cartridge cap disposed over the cartridge body and the reservoir.

14. The cartridge of claim 1, wherein the cartridge includes an identifier configured to convey information about the formulation or the cartridge to a device.

15. The cartridge of claim 1, further comprising the formulation stored in the reservoir.

16. The cartridge of claim 1, wherein the cartridge body includes an alignment structure configured to align the cartridge with a device.

17. The cartridge of claim 16, wherein the alignment structure of the cartridge body is a concave outer surface.

18. The cartridge of claim 1, wherein the reservoir includes a coupling structure configured to couple with a complementary coupling structure of a device.

19. The cartridge of claim 1, wherein a difference between the first rotational position and the second rotational position is between about 90 degrees and about 180 degrees.

20. A system, comprising:
a device; and
a cartridge configured for reversible coupling with the device, the cartridge being configurable between a closed state and an open state, the cartridge comprising:
a cartridge body having an outer locking element disposed thereon; and
a reservoir disposed in the cartridge body and being configured to store a formulation, the reservoir having a rotational locking element disposed thereon;
wherein in the closed state, the outer locking element of the cartridge body engages the rotational locking element of the reservoir such that the reservoir cannot be rotated out of a first rotational position relative to the cartridge body in which a fluid outlet of the reservoir is not in fluid communication with a fluid outlet of the cartridge body,
wherein in the open state, the outer locking element of the cartridge body does not engage the rotational locking element of the reservoir, and the reservoir is in a second rotational position relative to the cartridge body such that the fluid outlet of the reservoir is in fluid communication with the fluid outlet of the cartridge body.

* * * * *